United States Patent [19]

Zaiger

[11] Plant 4,110

[45] Sept. 20, 1977

[54] NECTARINE TREE

[76] Inventor: Chris Floyd Zaiger, 537 Rosemore Ave., Modesto, Calif. 95351

[21] Appl. No.: 719,668

[22] Filed: Sept. 1, 1976

[51] Int. Cl.[2] ..... A01H 5/03

[52] U.S. Cl. ..... Plt./41

[58] Field of Search ..... Plt./41

*Primary Examiner*—Robert E. Bagwill

[57] ABSTRACT

A variety of nectarine tree of medium to large size, vigorous growth and regular, productive bearing of medium size, yellow flesh, clingstone fruit, with a high degree of red skin color.

1 Drawing Figure

ORIGIN OF VARIETY

The herein claimed variety of nectarine tree was originated by me in my experimental orchard located near Modesto, Calif., as a second generation seedling of a cross between a seedling of Red Grand Nectarine (U.S. Plant Pat. No. 1,060) and Red June Nectarine (U.S. Plant Pat. No. 2,044). I maintained the selection under careful and continual observation during which time I recognized its distinct and desirable characteristics described above and selected the variety for reproduction.

ASEXUAL REPRODUCTION OF THE VARIETY

The present variety was asexually propagated by grafting and budding, as performed at Modesto, Calif., shows that said characteristics come true to form and are established and transmitted through succeeding propagation.

SUMMARY OF VARIETY

My new variety relates to a new and distinct variety of nectarine tree which bears yellow flesh, clingstone fruit, characterized as to its novelty by early ripening; ripening in late May in Modesto, Calif. The maturity date being 4 to 5 days earlier than the nectarine Red June, (U.S. Plant Pat. No. 2,044). My new variety is also characterized by having a high degree of red skin, uniform ripening, and a high degree of firmness. The attractive skin color, good flavor and shipping quality makes this variety a desirable nectarine for the commercial fruit industry.

BRIEF DESCRIPTION OF THE PHOTOGRAPH

The accompanying photographs show typical specimens of the foliage and fruit of my new variety, with upper and lower surfaces of the foliage being illustrated and exterior and a sectional view of the fruit being shown. The illustrations were taken shortly after being picked at maturity (shipping ripe) and the colors are as nearly true as reasonably possible in a color representation of this type.

DESCRIPTION OF THE VARIETY

The following is a detailed description of the foliage and fruit of my new variety, as based upon observations of specimens grown at Modesto, Calif., with color terminology in accordance with Reinhold Color Atlas by A. Kornerup and J. H. Wanscher.

Tree:
- *Size.*—Medium to large.
- *Vigor.*—Vigorous.
- *Form.*—Spreading.
- *Production.*—Productive.
- *Bearing.*—Regular.

Trunk:
- *Size.*—Medium.

Branches:
- *Size.*—Stocky to medium.

Leaves:
- *Size.*—Large to medium; average length 6 inches; average width 1½ inches.
- *Texture.*—Smooth.
- *Margin.*—Crenate.
- *Petiole.*—Medium length.
- *Glands.*—Usually 2 or more; medium size; reniform.
- *Color.*—Upper surface — greyish green (29-E-4) to (29-E-5). Lower surface — green (30-D-5) to (30-D-6).

Flower buds:
- *Size.*—Medium size; medium length.
- *Form.*—Plump.
- *Pubescence.*—Pubescent.

Flowers:
- *Size.*—Large.
- *Blooming period.*—Feb. 26, 1976 to Mar. 10, 1976 varies slightly with climatic conditions.
- *Pollen.*—Present.
- *Color.*—Pink, showy.

Fruit:
- *Maturity when described.*—Hard ripe.
- *Date of first picking.*—May 25, 1976.
- *Date of last picking.*—June 5, 1976.
- *Size.*—Medium; average diameter axially 2⅛" to 2½"; average transversely in suture plane 2⅛" to 2 9/16".
- *Form.*—Globose — nearly symmetrical.
- *Suture.*—Shallow.
- *Ventral surface.*—Rounded and only very slightly lipped.
- *Base.*—Retuse.
- *Cavity.*—Rounded; average depth — ⅜"; average breadth — ¾".
- *Apex.*—Rounded; varied from slight point to slight depression.

Skin:
- *Thickness.*—Medium.
- *Texture.*—Medium.
- *Tendency to crack.*—None.
- *Down.*—Wanting.
- *Color.*—Yellow (5-A-8) shading to (5-A-7) undercolor. Red blush covering most of the surface of the nectarine, shading from currant red (9-A-8) to cherry red (9-B-8).

Flesh:
- *Texture.*—Firm.

*Ripens.*—Even.
*Juice.*—Moderate.
*Flavor.*—Subacid to mild.
*Eating quality.*—Good.
*Color.*—Orange yellow (4-A-8) to deep chrome yellow (5-A-8).

Stone:
*Type.*—Clingstone.
*Size.*—Medium; average length — 1 3/16"; average breadth — 1"; average thickness — ¾".
*Tendency to split.*—Slight.
*Color.*—Brown (8-C-5 to 8-D-5).

Use: Dessert; Market — local and long distance shipping.
Keeping quality: Good.
Shipping quality: Good.

The nectarine tree and its fruit herein described may vary in slight detail due to climatic and soil conditions under which this variety may be grown; the present description being of the variety as grown in the Central Valley of California.

I claim:

1. A new and distinct variety of nectarine tree as illustrated and described, characterized by its early maturity of medium size, yellow fleshed, clingstone fruit. The skin of the fruit having a yellow ground color being nearly overspread completely with red and further characterized a vigorous, large tree of regular bearing early nectarines ripening 4 to 5 days before Red June (U.S. Plant No. 2,044).

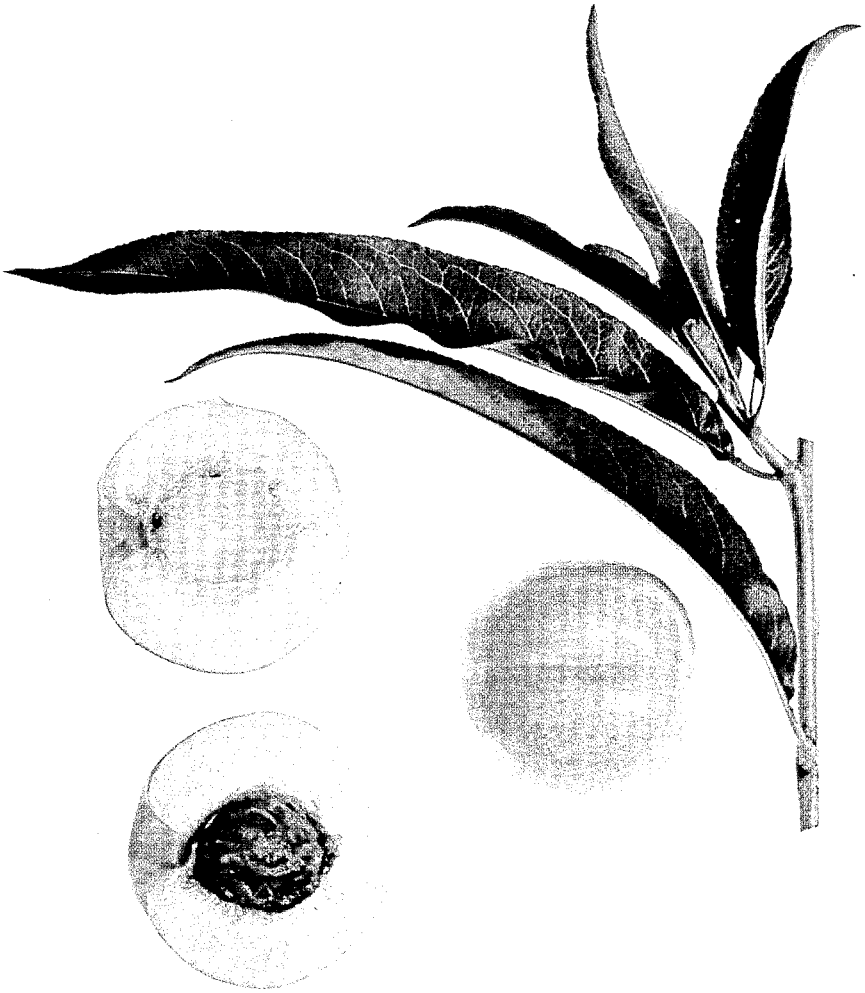

* * * * *